(12) United States Patent
Pike (10) Patent No.: US 7,099,437 B2
(45) Date of Patent: Aug. 29, 2006

(54) DOUBLE CRYSTAL ANALYZER LINKAGE

(75) Inventor: Timothy D. Pike, Gaithersburg, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/525,990

(22) PCT Filed: Sep. 22, 2003

(86) PCT No.: PCT/US03/29817

§ 371 (c)(1),
(2), (4) Date: Oct. 14, 2005

(87) PCT Pub. No.: WO2004/036174

PCT Pub. Date: Apr. 24, 2004

(65) Prior Publication Data

US 2006/0126787 A1    Jun. 15, 2006

(51) Int. Cl.
*G21K 1/06* (2006.01)
*G01N 23/20* (2006.01)

(52) U.S. Cl. ............................. 378/85; 378/84; 378/70
(58) Field of Classification Search ............ 378/70–85
See application file for complete search history.

(56) References Cited

U.S. PATENT DOCUMENTS

| | | | | |
|---|---|---|---|---|
| 3,906,225 | A * | 9/1975 | Guernet et al. | 378/82 |
| 4,472,825 | A | 9/1984 | Jenkins | |
| 4,752,945 | A | 6/1988 | Jenkins et al. | |
| 4,821,301 | A * | 4/1989 | Cocks et al. | 378/70 |
| 5,157,702 | A | 10/1992 | Middleton et al. | |
| 5,268,954 | A | 12/1993 | Middleton | |
| 5,444,242 | A * | 8/1995 | Larson et al. | 250/305 |
| 5,509,043 | A * | 4/1996 | Van Der Sluis | 378/85 |
| 5,850,425 | A * | 12/1998 | Wilkins | 378/85 |
| 5,892,809 | A * | 4/1999 | Wittry | 378/85 |
| 6,576,306 | B1 * | 6/2003 | Mehta et al. | 428/35.5 |

OTHER PUBLICATIONS

J. Golovchenko, et al.; x-Ray Monochromator System for Use With Synchrotron Radiation Sources; Rev. Sci. Instrum, 52(4), Apr. 1981; pp. 509-516.

C. Broholm; Proposal for a Doubly Focusing Cold Neutron Spectrometer at NIST;Nucl. Instr. and Methods in Physics Res. A 369 (1996) 169-179.

(Continued)

*Primary Examiner*—Edward J. Glick
*Assistant Examiner*—Irakli Kiknadze
(74) *Attorney, Agent, or Firm*—Whitham, Curtis, Christofferson & Cook, PC (57) ABSTRACT

A double crystal analyzer linkage includes the fixed pivot point, a fixed pivot point shaft, and three sliding axis points constrained to allow only sliding motion along given linear, parallel paths. The three paths are arranged such that one path passes through the fixed pivot point shaft on a central path and the two remaining paths are on opposite sides and equidistant from the central path. Two diffracting devices (200, 200') are mounted to axis points which traverse the outer paths (204, 204'). A right angle slide (210) constrains the two linear paths to only slide through a single axis point and constrains the two linear paths to be at right angles to each other. An inline slide constrains two paths to slide through a single axis point, and constrains the two paths to be parallel to each other. First (212) and second linkage (214) devices are connected to the right angle slide (210) and the two remaining axis points, and constrain the two diffracting devices (200, 200') to remain parallel at all times.

12 Claims, 11 Drawing Sheets

OTHER PUBLICATIONS

G. Jones et al; "Design and Performance of the Advanced Light Source Double-Crystal Monochromator"; Rev. Sci. Instrum. 66 (2), Feb. 1995; pp. 1748-1750.

P. Cowan et al; "A UHV Compatible Two-Crystal Monochromator for Synchrotron Radiation"; Nuc. Inst. and Meth. 208 (1983) 349-353.

* cited by examiner

DOUBLE CRYSTAL ANALYZER LINKAGE

BACKGROUND OF THE INVENTION

1. Field of the Invention

The present invention generally relates to spectrometry and, more particularly, to a linkage design used in a double crystal analyzer system.

2. Background Description

An "analyzer" is a spectrometer capable of measuring a single energy which can be scanned through a wide energy range. As used herein, "analyzers" go beyond simple frequency bandpass selection to include conditioning for topography, x-ray or neutron interferometry, x-ray or neutron standing waves, and phase selection. Analyzers covering the energy range from a few kilovolts and higher generally use single crystals of silicon or germanium as energy dispersive elements. Previously, Golovchenko et al. described an X-ray monochomator system for use with synchotron radiation sources (J. A. Golovchenko et al., *Rev. Sci. Instrum.* 52(4) April 1981). The Golovchenko system includes two separate Bragg reflecting crystals constrained by a mechanical linkage system. The design enables it to tune continuously in x-ray energies, while maintaining an exit beam of constant offset and direction relative to the incident beam.

Figure 1:
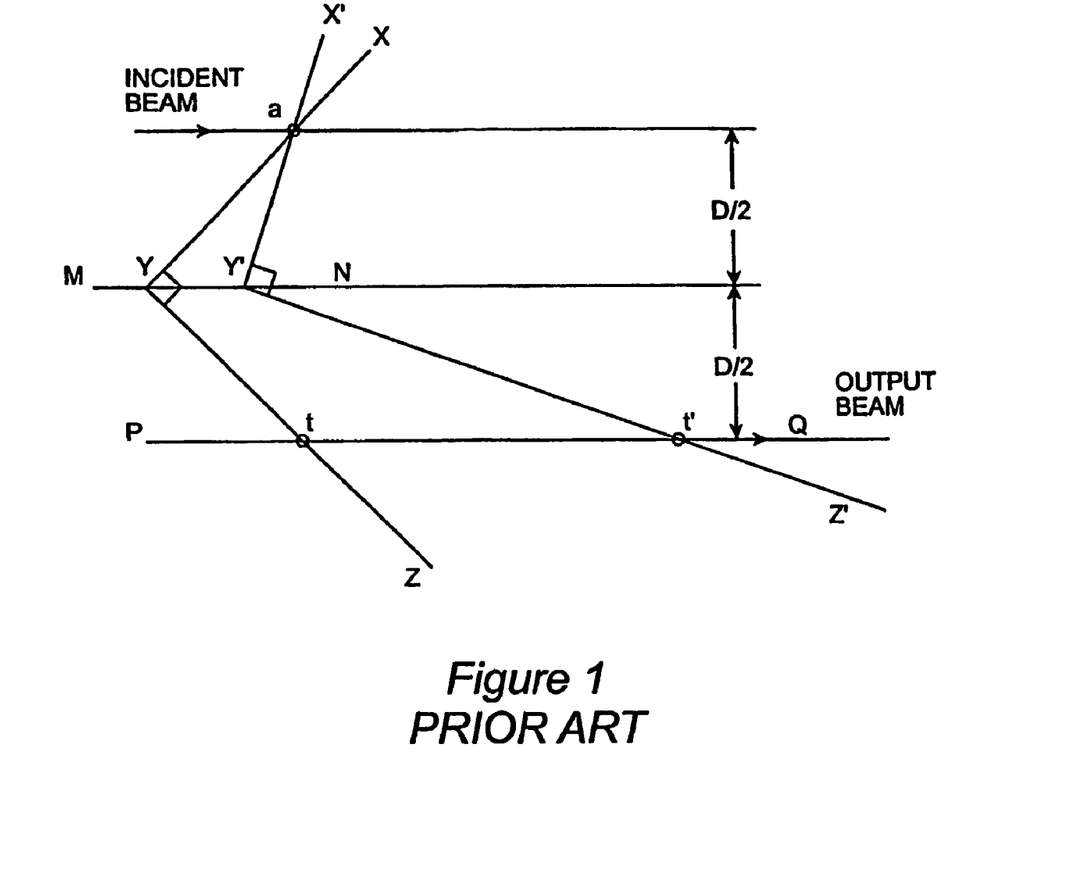
FIG. 1 is a schematic drawing illustrating a prior art configuration which shows the sliding and rotating motion of a rigid right angle.

FIG. 1 illustrates the "rigid right angle" concept of Golovchenko. Crystal positions are at a and b or a and b'. The concept of Golovchenko requires that the apex of the right angle Y must always have a vertical height exactly halfway between the height of the beam incident on the analyzer and the desired output beam height, and that the bar YX must always pass through some fixed position a at the incident beam height. The apex Y and second crystal at b are constrained to translate along parallel lines. For any given position of the apex Y along the midline MN, the rigid right angle must rotate about its apex Y in order that the length of YX intercept the fixed point a at the beam height.

Figure 2:
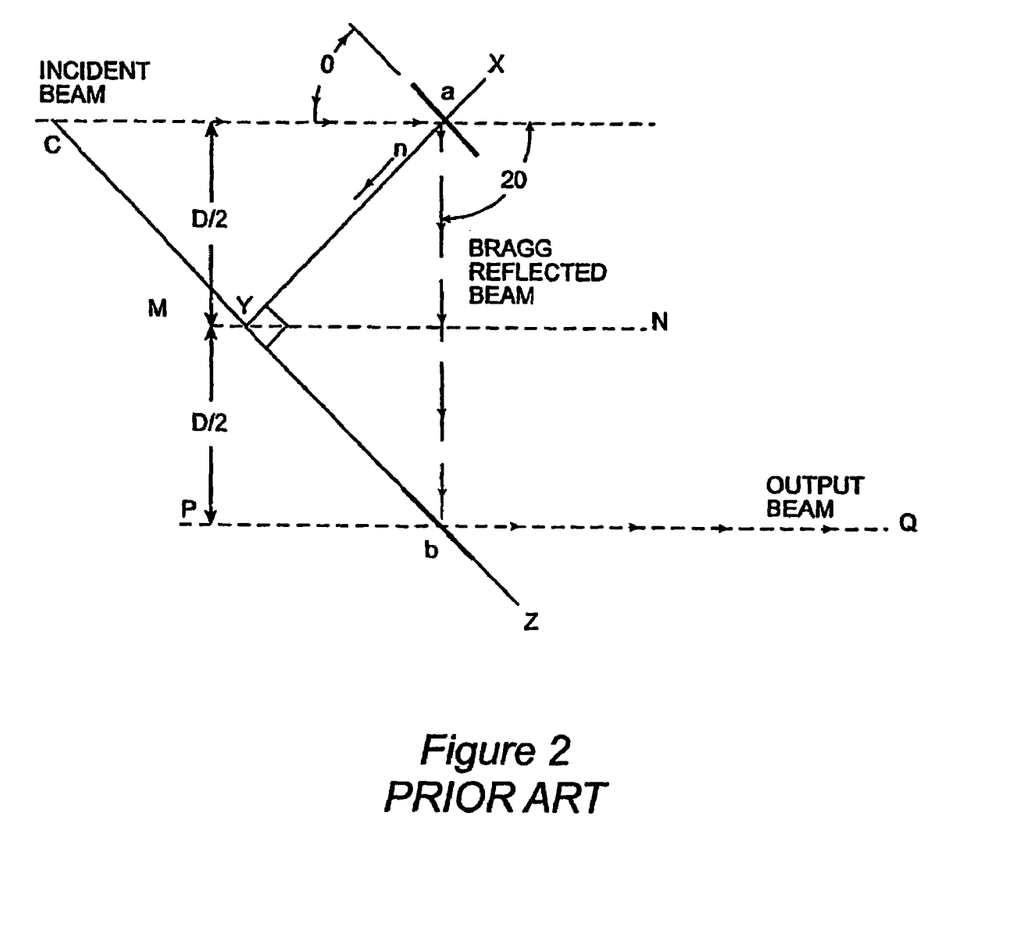
FIG. 2 is a schematic drawing of the prior art configuration of FIG. 1 which highlights the path of the beam through the two reflecting crystals.

Golovchenko indicated that the analyzer design acted as mechanical analogue computer generating proper crystal angles and displacements for the double crystal analyzer. With reference to FIG. 2, it can be seen that, depending on the planar spacing and angle of incidence θ, an energy will be selected by Braggs Law and the beam will be deflected by 2θ at a. Different positions of the apex Y along MN will yield different values of the angle of incidence θ, thereby permitting the system to have a mechanism to scanning through different selected energies. Thus, regardless of the energy chosen (as dictated by the horizontal position Y), the beam reflected from a will always intercept the bar YZ at the desired beam height. That is, the reflected beam, the bar YZ and the line PQ will always intercept each other at one point. This is proven by extending the line ZY to intercept the incident beam height at point c. The equality of incidence and reflection angles from the first crystal coupled with the congruence of triangles Yax and Yab yields the desired result.

Figure 3:
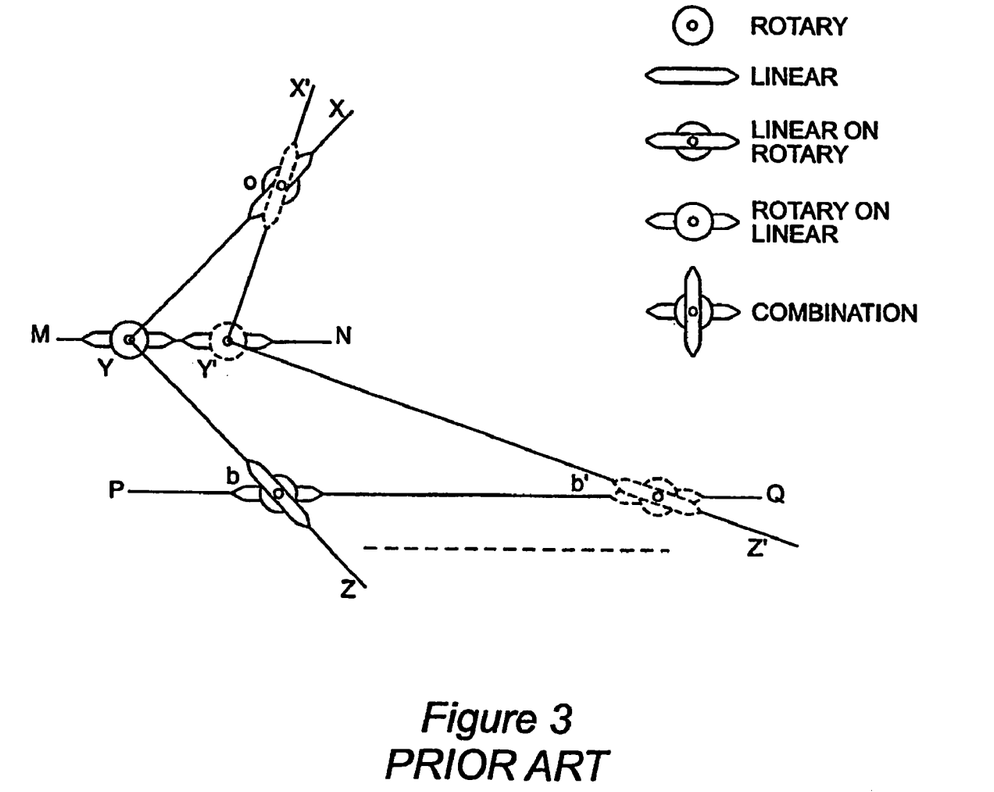
FIG. 3 is a schematic drawing illustrating the prior art configuration of FIG. 1 which highlights the motions required for operation of the linkage.

FIG. 3 provides a summary of motions required for operation of the Golovchenko linkage. In the x-ray analyzer system, bearing positions of low energy setting are drawn in solid (XYZ angle) and those for a higher energy setting are dashed (X'Y'Z' angle). To change energy, the rigid bar YX must slide through and rotate about point a. The linear bearing through which YX slides must therefore be mounted on a rotary bearing whose axis is at a perpendicular to the plane of FIG. 3. The first crystal is mounted directly over the linear bearing at a and perpendicular to YX. Another compound linear slide and rotary motion allows the apex Y to translate along rigid rod MN which is halfway between the incident beam height and exit beam height. Another bearing package slides on PQ. The combination contains two linear slide bearings joined by a rotary bearing. The second crystal mounts above the slide through which YZ passes and is oriented parallel to YZ.

P. L. Cowan et al., *Nuc. Inst. Meth.* 208:349–353 (1983), describes application of the Golovchenko et al. system for use in an ultra high vacuum (UHV) environment. The assembly is referred to as a "boomerang", and similar to the Golvchenko et al. design, the cross roller slides forbid any relative rotation of the two crystals, and the Bragg angle of both crystals is changed by rotating the "boomerang". Further, the linkage is completed by fixing one crystal axis and constraining the apex pivot and the second crystal axis to move along two equally spaced lined parallel to the incident radiation.

G. Jones et al., *Rev. Sci. Instrum.* 66(2) February 1995, describes a "Cowan type" double crystal analyzer based on the boomerang design which is used with advanced light source (ALS) that has a beam line covering the 1–6 keV photon-energy range. The design eliminates all of the bearings, and movement is accomplished using dovetail slides made of aluminum/bronze that slide on stainless steel bases.

SUMMARY OF THE INVENTION

It is therefore an object of the invention to provide a new double crystal analyzer linkage which can be used in a variety of applications including without limitation in the analysis of neutron scattering and in analyzers used with radiant energy (light, x-rays, etc.).

According to the invention, there is provided a double crystal analyzer linkage having a fixed pivot point and first, second and third sliding axis pivot points. The first, second and third sliding axis pivot points are constrained to move along spaced apart, parallel first, second and third linear pathways. The fixed pivot point is located on the third pathway between the first and second pathways. The distances between the first and third pathways and the second and third pathways are equal. The first and second movable axis pivot points have first and second means to secure first and second diffracting crystals so that centroids of the first and second diffracting crystals are located at respective ones of the first and second movable axis pivot points. A right angle slide movable along the third pathway has first and second pathways passing therethrough at right angles to, but spaced apart from one another, and passing through the third movable axis pivot points. First and second linkages slide in the first and second pathways of the right angle slide and are connected respectively to the first and second means to secure the first and second diffracting crystals so as to constrain planar surfaces of the diffracting crystals to remain parallel to one another as the first and second movable axis pivot points move along the first and second spaced apart, parallel linear pathways. An in-line slide is connected to and pivots about the fixed pivot point. The in-line slide has third and fourth pathways passing therethrough parallel to but spaced apart from one another. Third and fourth linkages slide in the third and fourth pathways, respectively, and are connected respectively to the first and second means to secure the first and second diffracting crystals so as to constrain the diffracting crystals to be equidistant from the fixed pivot point as the first and second movable axis pivot points move along said spaced apart, parallel linear pathways.

Selected energy diffracted from the first diffracting crystal is passed by a collimator to the second diffracting crystal. More particularly, a rotating rod passes through the fixed pivot point and rotates with the in-line slide as the in-line slide pivots about said fixed pivot point. The collimator is positioned along the central pathway, and a fifth linkage is connected between said rotating rod and the collimator, said fifth linkage rotating said collimator so as to pass energy diffracted from the first diffracting crystal to the second diffracting crystal as the first and second sliding axis pivot points are slid along respective ones of the spaced apart, parallel linear pathways. The collimator comprises a plurality of vanes parallel to one another and rotating about parallel axes at one half an angle of rotation of the first and second diffracting crystals as the first and second sliding axis pivot points are slid along respective ones of the spaced apart, parallel linear pathways.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 4:
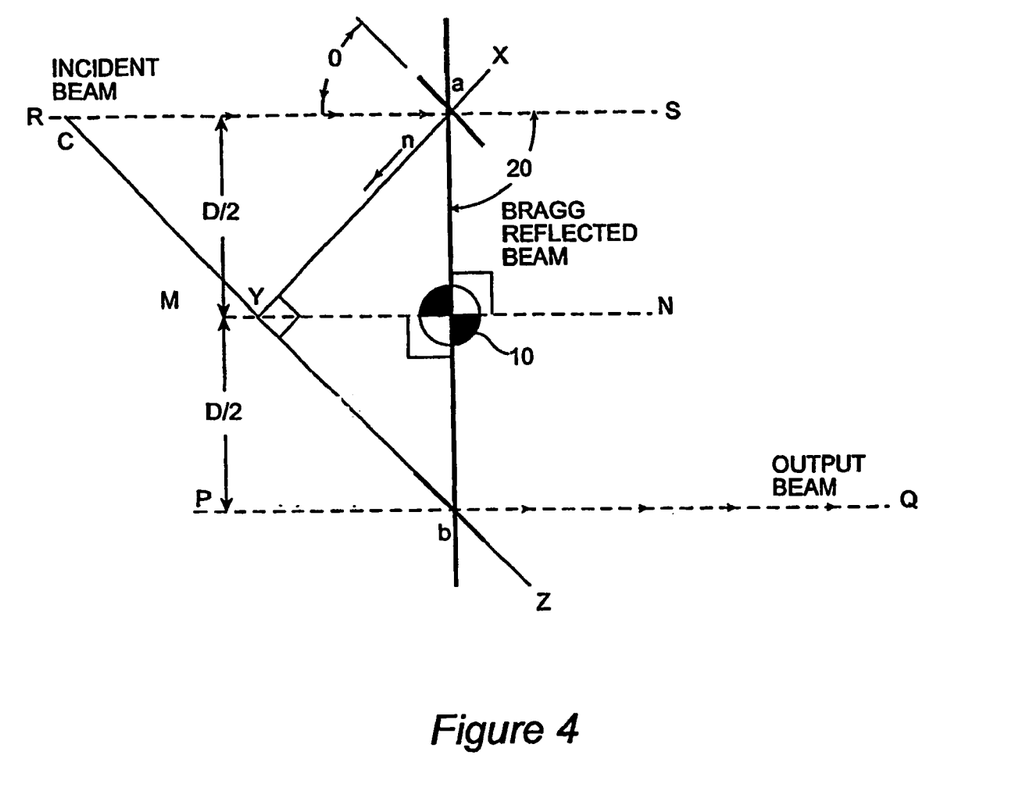
FIG. 4 is a schematic drawing illustrating the present invention showing the fixed pivot point in line with a path traveled by the right angle slide.
Figure 5:
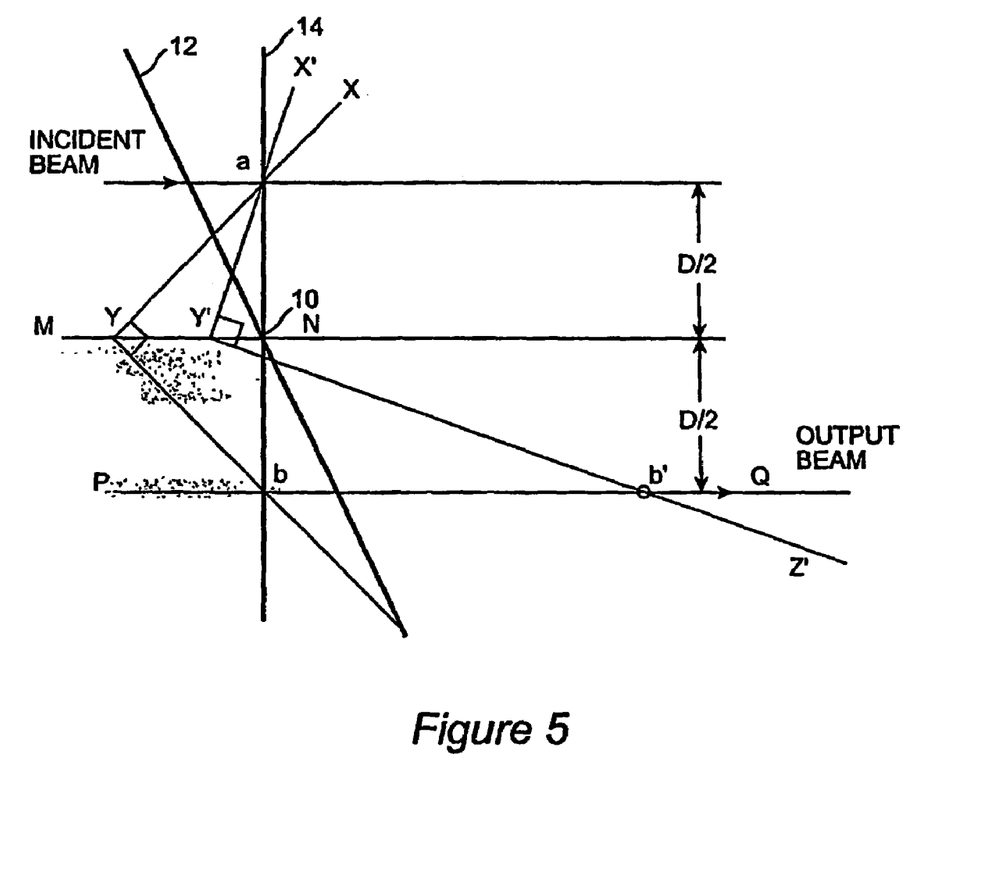
FIG. 5 is a schematic drawing illustrating the present invention showing how the right angle relationship between the diffracting devices is maintained while allowing movement of both diffracting devices and the right angle slide.

Referring now to the drawings, and more particularly to FIGS. 4 and 5, there are shown schematics drawing similar to the Golovchenko et al. concept depicted in FIGS. 2 and 1, respectively. However, the present invention contemplates having a fixed pivot point 10 on line MN which is positioned between the diffraction devices located at points a and b. In the present invention, point a is movable along path RS, point b is movable along path PQ, and the apex Y is movable along path MN. Unlike the Golovchenko et al. and the Cowan et al. "boomerang" design, point a is not constrained. In the practice of this invention, constraining point a is not a requirement for maintaining the precise parallel orientation of the diffraction devices located at points a and b. In the present invention, each of the points a, b and Y are each movable, rotational axes. As in the Golovchenko et al. design, the present invention maintains a precise parallel arrangement of the double diffraction devices, and maintains a precise offset of the incident beam from the output beam. FIG. 5 is similar to FIG. 1, however it shows lines 12 and 14 intersecting at a fixed pivot point 10 contemplated by the present invention.

Figure 6:
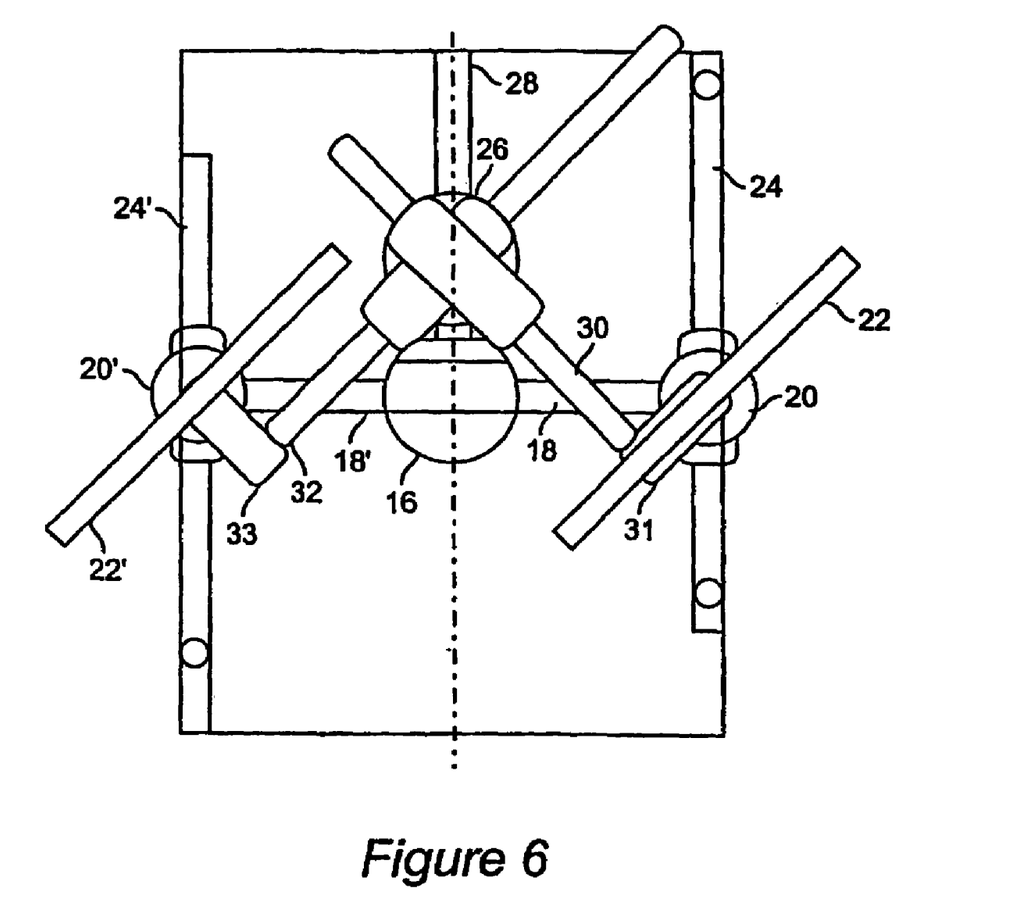
FIG. 6 is a plan view showing the conceptual mechanism of the linkage of the present invention.
Figure 7:
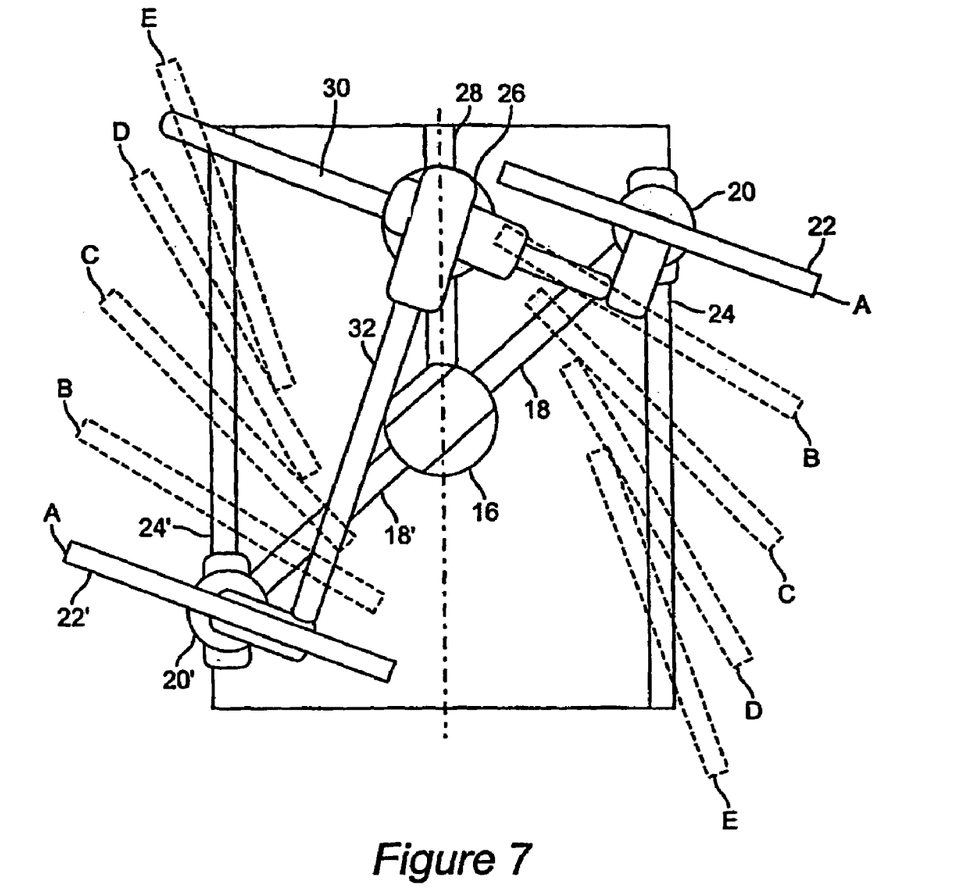
FIG. 7 is a plan view, similar to FIG. 6, showing different positions of the sliding elements and diffraction devices according to the present invention.

FIGS. 6 and 7 show a conceptual drawing of the invention with an inline slide 16 mechanically linked by rods 18 and 18' to devices 20 and 20' for holding the diffraction devices 22 and 22'. The diffraction devices 22 and 22' are typically made of the same material, but in some applications different materials may be used. Typically, in applications involving the analysis of scattered neutrons, the diffraction devices will be graphite or copper. In x-ray applications, many different crystalline materials may be suitable, including silicon and germanium crystals. In some applications, the diffraction devices can be simple mirrors (i.e., polished silver).

In the present invention, devices 20 and 20' rotate, and have an axis of rotation which passes through the midpoint or geometric centroid of a connected diffracting device 22 or 22' and which is normal to the plane of FIG. 6. The axis of rotation for devices 20 and 20' corresponds to points a and b in FIGS. 4 and 5. The devices 20 and 21' travel along parallel outer pathways 24 and 24', respectively, such as by sliding or other suitable means of movement. The inline slide 16 is located at and pivots about a fixed pivot point. A right angle slide 26 is moveable along a central pathway 28 which passes through the fixed pivot point. The right angle slide 26 has an axis of rotation that is parallel to the axes of rotation for devices 20 and 20', and which corresponds to the apex Y in FIGS. 4 and 5.

The right angle slide 26 includes paths extending therethrough, at different vertical heights, which accommodate the first and second linkage rods 30 and 32. First and second linkage rods 30 and 32 slide in the right angle slide 26. The first and second linkage rods 30 and 32 are connected to the devices 20 and 20' by means of respective bell cranks 31 and 33. The connection is such as to constrain opposing planar surfaces of the diffracting devices 22 and 22' to be parallel to one another. This is shown in FIG. 7 where, as the devices 20 and 20' move along pathways 24 and 24' and the right angle slide 26 moves along pathway 28, the opposing planar surfaces of the diffracting devices 22 and 22' are maintained in parallel relation, as indicated at a varying positions A–E noted by the dashed lines. From FIG. 7, it should be clear that the movable or "sliding" axis points at devices 20 and 20' and right angle slide 26 move in a coordinated fashion whereby they each slide on their respective pathways 24, 24' and 28, and each rotate about their vertical axis, at the same time. During this movement and rotation, the first and second linkage rods 30 and 32 slide within the right angle slide 26 and assure that the diffraction devices 22 and 22' are maintained parallel by rotating the devices 20 and 20'.

Figure 10:
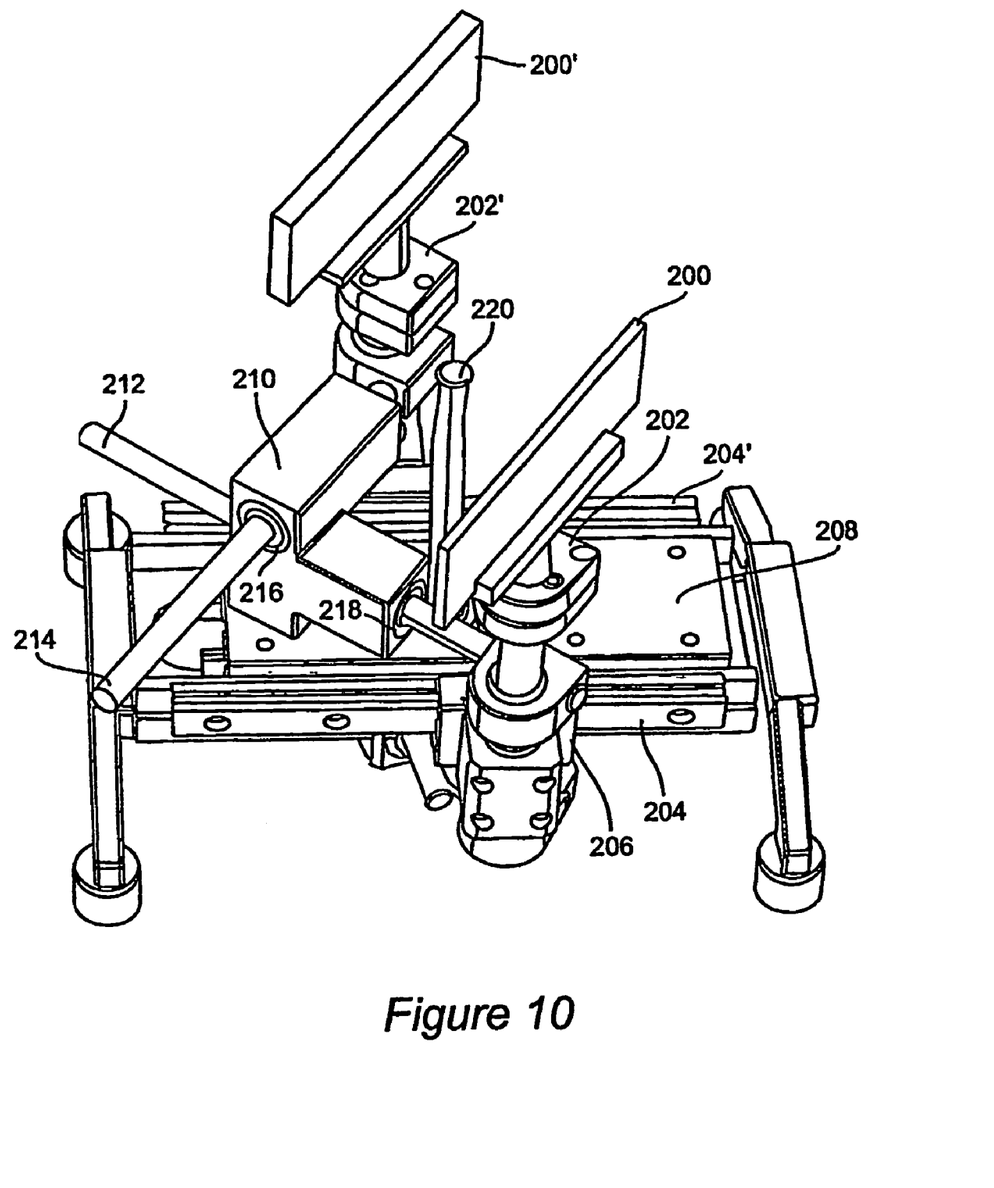
FIG. 10 is an isometric top view of a preferred embodiment of the present invention.
Figure 11:
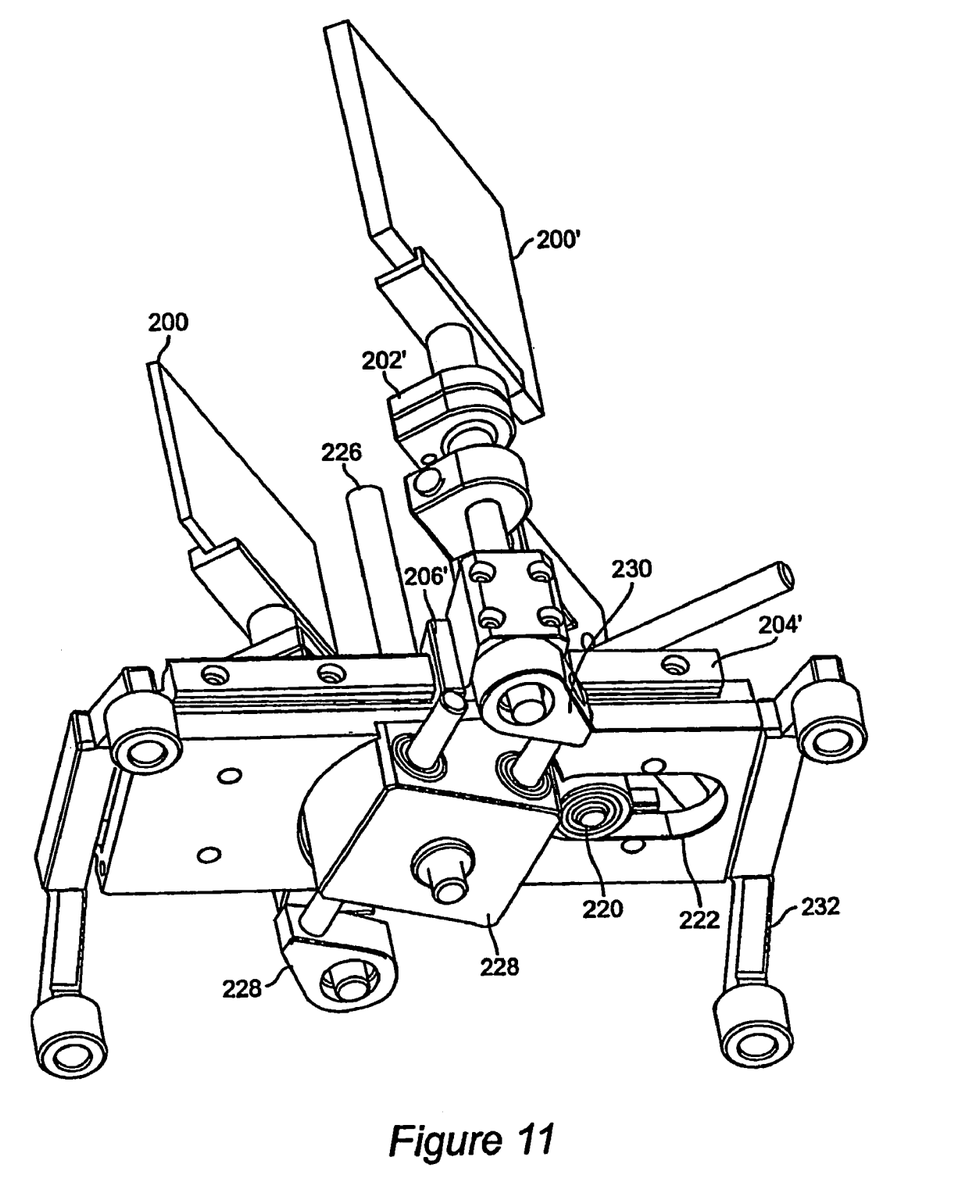
FIG. 11 is an isometric bottom view of a preferred embodiment of the present invention.
Figure 12:
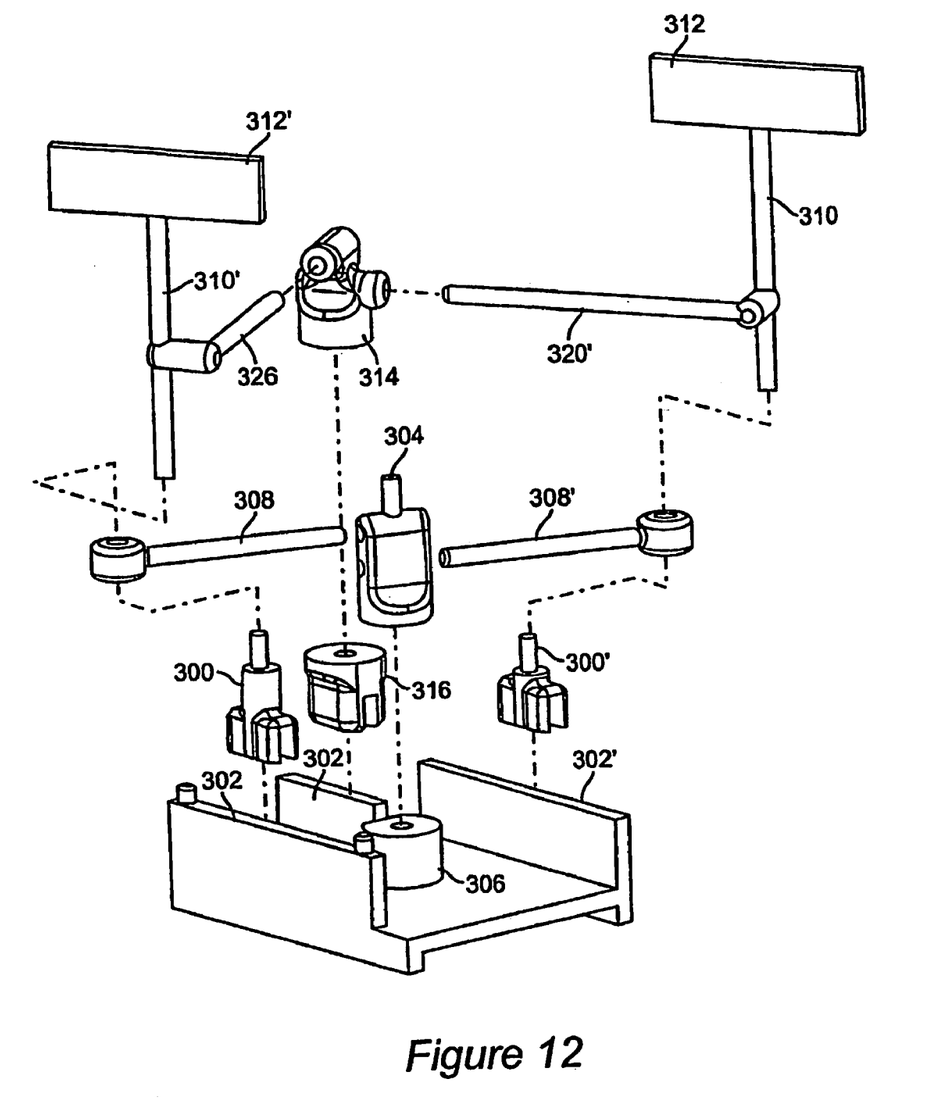
FIG. 12 is an exploded view of the components used in a second preferred embodiment of the present invention.

The axis point of the in-line slide 16 is coincident with the fixed pivot point (shown as 10 in FIG. 4), and is constrained to rotation about the fixed pivot point. The linkage rods 18 and 18' slide within the inline slide 16 depending on the location of the devices 20 and 20'. As will be discussed below, the rods 18 and 18' can be positioned over top of one another as shown in FIG. 12 or can be side by side as shown in FIG. 11. A stepper motor or other precision driving mechanism can be connected to a shaft (not shown in FIG. 7, but which is shown in FIG. 10) to drive the mechanism either incrementally or continuously. Specifically, for example, counter-clockwise rotation of the shaft causes the rod 18 to slide outwardly as device 20 slides along pathway 24 and causes the rod 18' to slide outwardly as device 20' slides along pathway 24'. In a corresponding action, the first linkage rod 30 slides within right angle slide 26, and the second linkage rod 32 slides outwardly from right angle slide 26. The movements are constrained by passages in the right angle slide 26 and the inline slide 16, as well as by the fixed pathways 24, 24' and 28 along which the devices 20 and 20' and the right angle slide 26 move. The diffraction devices 22 and 22' are kept parallel at all times, and are moved to a variety of locations to accommodate different light angles or energies.

Figure 8:
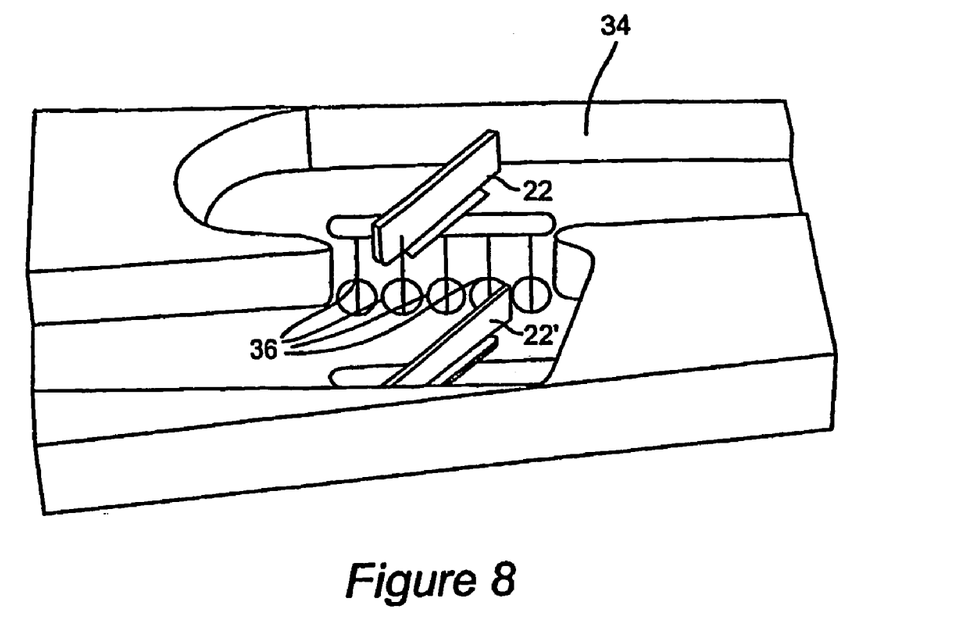
FIG. 8 is a perspective view showing a collimator positioned between the diffraction devices according to the present invention.
Figure 9:
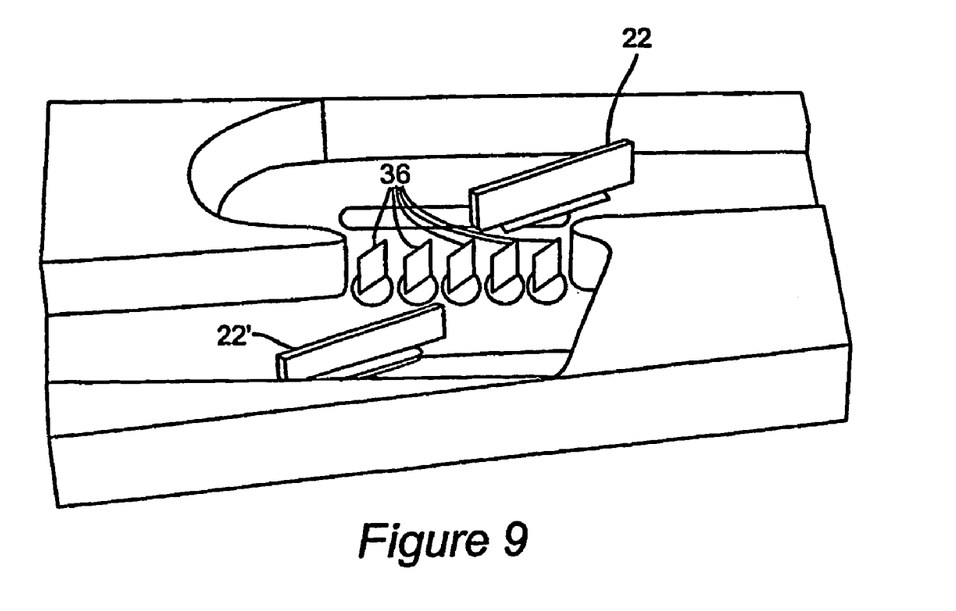
FIG. 9 is a perspective view, similar to FIG. 8, which shows the diffraction devices moved along their parallel pathways with the collimator positioned therebetween being rotated to a different position.

FIGS. 8 and 9 show an embodiment of the invention which includes a collimator depicted as louvers or vanes 36 positioned between the diffraction devices 22 and 22'. The vanes 36 can be made of a variety of materials (e.g., metals, ceramics, etc.) and function to stop stray energy (light, neutrons, x-rays, other radiant energy) from being passed. Stray energy can arise from a number of sources including without limitation, energy which reflects off wall 34 at an unintended angle towards diffraction device 22', energy which reflects off an unintended crystalline plane or incongruity in the crystalline diffraction device 22', and energy which is directed at diffraction device 22' at a non-desired angle. As can be seen by the different angles of the vanes 36 shown in FIGS. 8 and 9, stray energy will not pass between the diffraction devices 22 and 22'. The height and thickness of the vanes 36, as well as the number of vanes 36 can vary within the practice of this invention.

In a preferred embodiment, the vanes 36 are connected to and driven by a shaft which passes through the fixed pivot point rotate as the diffraction devices 22 and 22' translate along pathways 24 and 24'. Specifically, the vanes will rotate about parallel axes at one half an angle of rotation of the diffraction devices. In this way, as the angle of the diffraction devices 22 and 22' are changed (it being understood that the faces of the diffraction devices remain parallel as discussed above), the angle of the vanes 36 is changed. Preferably, the angle of the vanes 36 is changed to be parallel to the intended direction of the energy reflected from the diffraction device 22. This eliminates stray energy, and, simultaneously results in minimal (if any) attenuation of the energy (neutrons, x-rays, etc.) intended to pass between the diffraction devices 22 and 22'.

FIGS. 10 and 11 depict a preferred embodiment of the invention, and FIG. 12 shows an exploded view and alternative embodiment.

In FIGS. 10 and 11, the diffraction devices 200 and 200' are copper or graphite. The diffraction devices are secured on movable axis pivot devices 202 and 202; which are constrained to translate along parallel pathways 204 and 204'. The pathways 204 and 204' preferably take the form guide rods to which sliding connectors 206 and 206' are respectively attached. A centrally located platform 208 includes a right angle slide 210 connected thereto. As discussed above, the right angle slide 210 rotates about a vertical axis of rotation. First and second linkage rods 212 and 214 pass through channels 216 and 218 in the right angle slide 210. The vertical axis of rotation in the right angle slide 210 is coincident with an intersection of vertical planes which would align with the linkage devices 212 and 214. The linkage rods 212 and 214 are maintained at a right angle at all times. The linkage rods 212 and 214 are connected to the movable pivot devices 202 and 202'. In this way, movement of the diffraction devices 200 and 200' and right angle slide 210 is always achieved in a fashion where the diffraction devices 200 and 200' are maintained in parallel orientation.

With reference to FIG. 11, it can be seen that a cam 220 and slot 222 can be used to allow translation of the right angle slide 210 on a central pathway that is parallel to the guide rods 204 and 204'. A fixed pivot point shaft 226 can be driven by a stepper motor or other precision device. In this way, the diffraction devices 200 and 200' can be pivoted to select for a plurality of energy levels or wavelengths with extremely high precision. As discussed above, a monochomator, or other attenuating device (not shown) can be mounted on the fixed pivot point shaft 226. In the embodiment shown in FIG. 11, a rotatable block 228 is connected to the fixed pivot point shaft 226, and rod and follower assemblies 228 and 230 are connected to the pivot devices 202 and 202'. In this way, as the fixed pivot point shaft 226 is rotated, the pivot devices 202 and 202', as well as the right angle slide 210 will slide on guide rails 204 and 204' and within slot 222, and, in addition, the pivot devices 202 and 202' and right angle slide 210 will rotate about their vertical axes. The angle of rotation input at the fixed pivot point shaft precisely reflects the angle that the incident beam impinges on the diffraction device 200. In this way, computational control of the double crystal analyzer linkage is simplified and made precise. Legs 232 can be used elevate the double crystal analyzer linkage so as to accommodate the rotatable block 228.

Contrasting FIGS. 10 and 11 with FIG. 4, the fixed pivot point shaft 220 corresponds to point 10, and the axes of rotation through the centroid or "midpoint" of the diffraction devices 200 and 200' correspond to points a and b, and the axis of rotation in the right angle slide 210 corresponds to vertex Y.

FIG. 12 is an exploded view showing the construction of the invention. In addition, FIG. 12 shows a variation on the preferred embodiment. Most notably, rotatable sliding members 300 and 300' slide on parallel rails 302 and 302'. The rotatable sliding members 300 and 300' are rotatable about a vertical axis. An in-line slide member 304 located at the fixed pivot point is positioned on pedestal 306 between the rails 302 and 302'. Linkage rods 308 and 308' pass through the in-line slide member 304 in a vertical relationship (as opposed to the side-by-side relationship illustrated in FIG. 11), and serve to constrain the sliding members 300 and 300' to slide along parallel rails 302 and 302'. Support members 310 and 310' are respectively connected to the rotatable sliding members 300 and 300'. Diffraction crystals or "diffraction devices" 312 and 312' are secured atop respective support members 310 and 310'.

A right angle slide member 314 is positioned atop sliding bearing 316 which is translatable along center pathway 318. As discussed above, the right angle slide member 314 is rotatable about a vertical axis. Linking rods 320 and 320' pass through passages in the right angle slide member 314. The passages in the right angle slide member 314 and the linking member 320 and 320' constrain the diffraction devices 312 and 312' to remain parallel at all times.

While the invention has been described in terms of a single preferred embodiment, those skilled in the art will recognize that the invention can be practiced with modification within the spirit and scope of the appended claims.

What is claimed is:

1. A double crystal analyzer linkage, comprising:
   a fixed pivot point;
   first, second and third sliding axis pivot points constrained to move along spaced apart, parallel first, second and third linear pathways, said fixed pivot point being located on said third pathway between said first and second pathways, distances between said first and third pathways and said second and third pathways being equal;
   said first and second movable axis pivot points having, respectively, first and second means to secure first and second diffracting crystals so that centroids of said first and second diffracting crystals are located at respective ones of said first and second movable axis pivot points;
   a right angle slide which is movable along said third pathway, said right angle slide having first and second pathways passing therethrough at right angles to but spaced apart from one another and passing through said third movable axis pivot points;
   first and second linkages sliding in said first and second pathways of said right angle slide and connected respectively to said first and second means to secure said first and second diffracting crystals so as to constrain planar surfaces of said diffracting crystals to remain parallel to one another as said first and second movable axis pivot points move along said first and second spaced apart, parallel linear pathways;
   an in-line slide connected to and pivoting about said fixed pivot point, said in-line slide having third and fourth pathways passing therethrough parallel to but spaced apart from one another; and
   third and fourth linkages sliding in said third and fourth pathways, respectively, and connected respectively to said first and second means to secure said first and second diffracting crystals so as to constrain said diffracting crystals to be equidistant from said fixed pivot point as said first and second movable axis pivot points move along said spaced apart, parallel linear pathways.

2. The double crystal analyzer linkage recited in claim 1, further comprising:
   a rotating rod passing through said fixed pivot point and rotating with said in-line slide as said in-line slide pivots about said fixed pivot point;
   collimator means positioned along said central pathway; and
   a fifth linkage connected between said rotating rod and said collimator means, said fifth linkage rotating said collimator means so as to pass radiation diffracted from said first diffracting crystal to said second diffracting crystal as said first and second sliding axis pivot points are slid along respective ones of said spaced apart, parallel linear pathways.

3. The double crystal analyzer linkage as recited in claim 2, wherein said collimator means comprises a plurality of vanes parallel to one another and rotating about parallel axes at one half an angle of rotation of first and second diffracting crystals as said first and second sliding axis pivot points are slid along respective ones of said spaced apart, parallel linear pathways.

4. The double crystal analyzer linkage recited in claim 1, wherein said first and second linkages include first and second bell cranks respectively attached to said first and second means to secure first and second diffracting crystals, said bell cranks rotating said first and second means to secure first and second diffracting crystals about respective ones of said first and second sliding axis pivot points as said first and second sliding axis pivot points move along said spaced apart, parallel linear pathways.

5. The double crystal analyzer linkage recited in claim 1, wherein said third and fourth pathways are in a plane parallel to a plane containing said spaced apart, parallel linear pathways and said third and fourth linkages include first and second attachment points offset from respective ones of said first and second sliding axis points.

6. The double crystal analyzer linkage recited in claim 1, wherein said third and fourth pathways are in a plane vertical to a plane containing said spaced apart, parallel linear pathways and said third and fourth linkages are connected to respective points passing through said first and second sliding axis pivot points.

7. The double crystal analyzer linkage recited in claim 1, wherein said first and second linkages include first and second bell cranks respectively attached to said first and second means to secure first and second diffracting crystals, said bell cranks rotating said first and second means to secure first and second diffracting crystals about respective ones of said first and second sliding axis pivot points as said first and second sliding axis pivot points move along said spaced apart, parallel linear pathways and wherein said third and fourth pathways are in a plane parallel to a plane containing said spaced apart, parallel linear pathways and said third and fourth linkages include first and second attachment points offset from respective ones of said first and second sliding axis points.

8. The double crystal analyzer linkage recited in claim 7, further comprising:
   a rotating rod passing through said fixed pivot point and rotating with said in-line slide as said in-line slide pivots about said fixed pivot point;
   collimator means positioned along said central pathway; and
   a fifth linkage connected between said rotating rod and said collimator means, said fifth linkage rotating said collimator means so as to pass radiation diffracted from said first diffracting crystal to said second diffracting crystal as said first and second sliding axis pivot points are slid along respective ones of said spaced apart, parallel linear pathways.

9. The double crystal analyzer linkage as recited in claim 8, wherein said collimator means comprises a plurality of vanes parallel to one another and rotating about parallel axes at one half an angle of rotation of first and second diffracting crystals as said first and second sliding axis pivot points are slid along respective ones of said spaced apart, parallel linear pathways.

10. The double crystal analyzer linkage recited in claim 1, wherein said first and second linkages include first and second bell cranks respectively attached to said first and second means to secure first and second diffracting crystals, said bell cranks rotating said first and second means to secure first and second diffracting crystals about respective ones of said first and second sliding axis pivot points as said first and second sliding axis pivot points move along said spaced apart, parallel linear pathways and wherein said third and fourth pathways are in a plane vertical to a plane containing said spaced apart, parallel linear pathways and said third and fourth linkages are connected to respective points passing through said first and second sliding axis pivot points.

11. The double crystal analyzer linkage recited in claim 10, further comprising:
- a rotating rod passing through said fixed pivot point and rotating with said in-line slide as said in-line slide pivots about said fixed pivot point;
- collimator means positioned along said central pathway; and
- a fifth linkage connected between said rotating rod and said collimator means, said fifth linkage rotating said collimator means so as to pass radiation diffracted from said first diffracting crystal to said second diffracting crystal as said first and second sliding axis pivot points are slid along respective ones of said spaced apart, parallel linear pathways.

12. The double crystal analyzer linkage as recited in claim 11, wherein said collimator means comprises a plurality of vanes parallel to one another and rotating about parallel axes at one half an angle of rotation of first and second diffracting crystals as said first and second sliding axis pivot points are slid along respective ones of said spaced apart, parallel linear pathways.

* * * * *